United States Patent [19]

McMahon et al.

[11] Patent Number: 5,467,763
[45] Date of Patent: Nov. 21, 1995

[54] SURGICAL INSTRUMENTS

[76] Inventors: Michael J. McMahon, 5 Foxhill Crescent, Leeds, West Yorkshire, England, LS16 5PD; Peter Moran, 31 Spring Valley Drive, Leeds, West Yorkshire, England, LS13 4RN

[21] Appl. No.: 277,699

[22] Filed: Jul. 20, 1994

Related U.S. Application Data

[63] Continuation of Ser. No. 942,674, Sep. 9, 1992, abandoned.

[30] Foreign Application Priority Data

Jan. 21, 1992 [GB] United Kingdom ............ 9201214
Jul. 30, 1992 [GB] United Kingdom ............ 9216233

[51] Int. Cl.⁶ .................................................. A61M 25/00
[52] U.S. Cl. ........................ 600/201; 606/170; 606/208; 604/164
[58] Field of Search ................. 128/3, 751, 20, 128/753.54; 606/170, 174, 209–211; 604/19, 27, 36, 93, 158, 164

[56] References Cited

U.S. PATENT DOCUMENTS

| | | |
|---|---|---|
| 2,079,233 | 5/1937 | Wappler. |
| 3,190,286 | 6/1965 | Stokes. |
| 3,642,352 | 2/1972 | Beach. |
| 3,799,151 | 3/1974 | Fukaumi et al.. |
| 3,958,576 | 5/1976 | Komiya .................... 606/174 |
| 4,226,228 | 10/1980 | Shin et al. ................ 128/20 |
| 4,239,036 | 12/1980 | Krieger .................... 128/20 |
| 4,483,562 | 11/1984 | Schoolman .............. 606/174 |
| 4,754,909 | 7/1988 | Barker et al.. |
| 4,950,273 | 8/1990 | Briggs .................... 606/174 |
| 4,982,727 | 1/1991 | Sato ........................ 606/205 |
| 5,035,248 | 7/1991 | Zinnecker ............... 606/205 |
| 5,152,779 | 10/1992 | Sanagi .................... 606/205 |

*Primary Examiner*—C. Fred Rosenbaum
*Assistant Examiner*—Perry E. Van Over
*Attorney, Agent, or Firm*—Thomas R. Vigil; John G. Bisbikis

[57] ABSTRACT

A surgical instrument includes a plurality of segments which can be moved relative to each other from a first position in which the segments extend in a straight direction and can be inserted through an opening in a body to a second position in which segments are brought tight against each other to cause the instrument to go round a bend. The segments are brought tight against each other by pulling a flexible element extending through the segments from a part of the instrument located outside of the body. Scissors or gripping means may be located at the free end of the instrument within the body, and these scissors or gripping means may be operated from outside of the body.

19 Claims, 10 Drawing Sheets

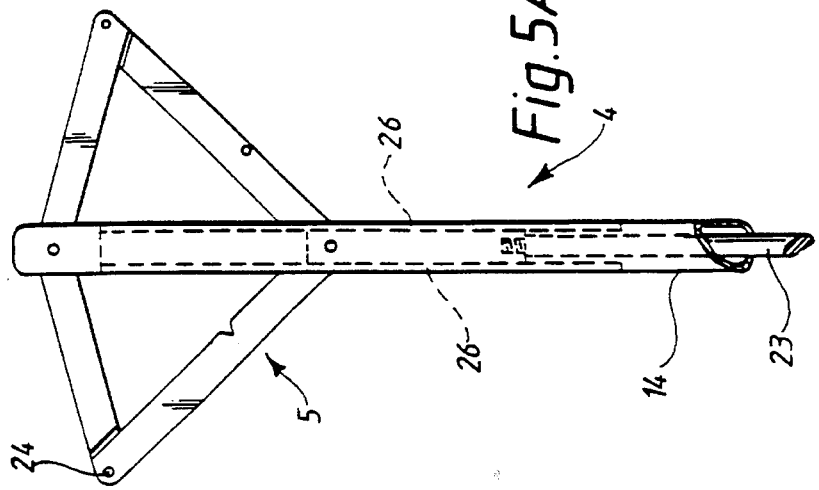
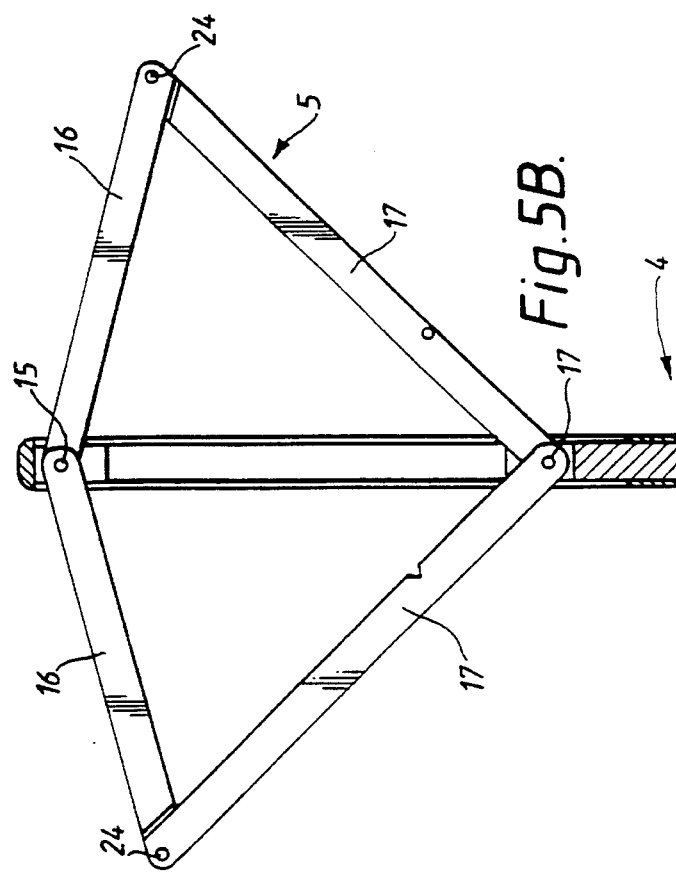
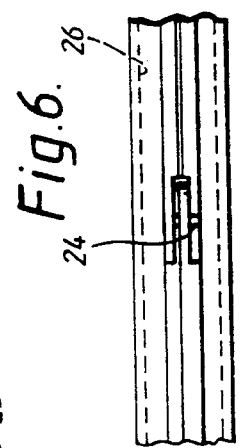

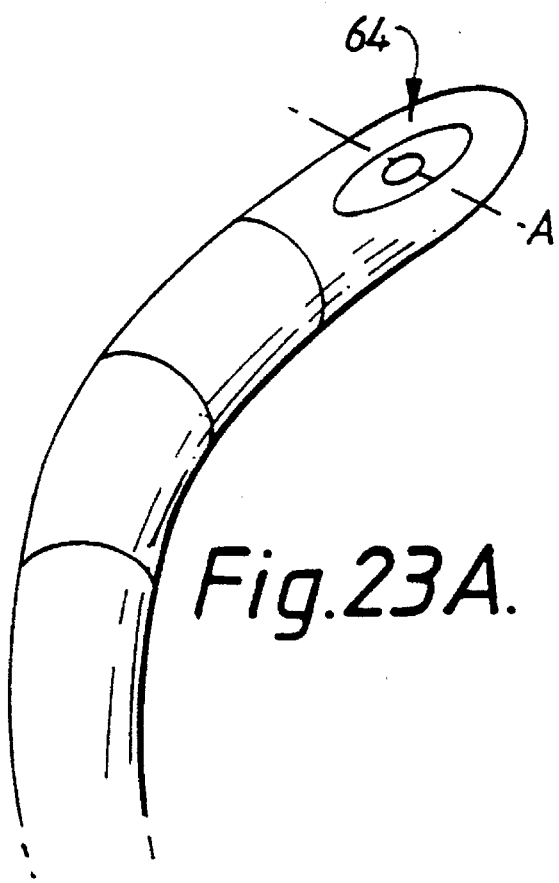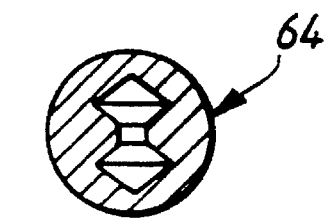
Fig.23A.
Fig.23B.

SURGICAL INSTRUMENTS

This is a continuation of application Ser. No. 07/942,674 filed Sept. 9, 1992, now abandoned.

TECHNICAL FIELD

The present invention relates to surgical instruments and to a method of operating surgical instruments.

BACKGROUND ART

In abdominal surgery it is possible for a surgeon to examine or operate on abdominal organs without the physical insertion of the surgeons fingers. This is done by making a hole through the skin and other tissues in order to enter a body cavity, blowing inert gas under pressure into the abdominal cavity through that hole to create space, and inserting an endoscopic camera through that opening so that the surgeon can view the organs on a remote monitor. Other tubes are then placed in the abdominal wall (usually of 5–11 mm diameter), which are sealed to prevent or restrict the egress of the inert gas, and instruments can then be inserted through these tubes. The instruments can either be for operating on the organs or for pushing organs out of the way, and the surgeon is able to manipulate them from outside of the body.

As the tubes are of restricted diameter (usual maximum 11 mm all that can be inserted through the tubes is a relatively straight instrument having a diameter of slightly less than the tube through which it is inserted. Thus, where a surgical retractor is used, the surgeon must displace organs and retain them in a displaced position with the use of a straight rod. It is difficult to so displace and retain the organs with such a straight rod and the organs are prone to slipping over the end of the rod thereby impeding the operation.

The surgical instruments described herein aim to reduce the problems associated with this type of surgery.

DISCLOSURE OF THE INVENTION

According to one aspect of the present invention, a surgical retractor includes an end portion movable from a first position in which, in use, the end portion and an intermediate portion of the retractor are able to be inserted in a generally linear direction through a restricted opening into a body cavity to a second position in which the end portion is not able to be inserted in a generally linear direction through the restricted opening in the body cavity, the end portion being movable from the first to the second position upon operation of an actuator of the retractor arranged, in use, to be located on the outside of a restricted opening into a body cavity.

The actuator may comprise a lever movable between two positions.

The actuator may comprise a rotatable member arranged to cause translational movement as a result of that rotation.

The retractor may include a connector connected to the actuator and the end portion and the connector may be directly connected to at least one or both of the actuator and the end portion. The connector may be slidable within the retractor. The connector may be rigid. Alternatively or additionally, at least a part of the connector may be flexible and the connector may include two flexible portions arranged to be co-extensive. The flexible connector may comprise a loop, for instance of wire.

The flexible connector may extend through a plurality of segments comprising the end portion. Adjacent segments may be arranged to co-operate, for instance directly, with each other in the second position. The segments may be arranged to be biased towards each other in the second position.

At least one, and preferably a plurality of the segments may include a co-operating portion which extends at an angle, which may be other than 90° C., to the general longitudinal extent of the retractor when in the first position. The co-operating portion may be caused to abut an adjacent portion in the second position. Adjacent segments may each include a co-operating portion which extends at an angle to the general longitudinal extent of the retractor when in the first position, and both ends of at least one segment may include such a co-operating portion. The extent of at least two co-operating portions may be generally parallel when in the first position. The extent of at least two other cooperating portions may also be parallel, but in a different direction to the other two parallel co-operating portions when in the first position.

In the first position a flexible member may connect a plurality of segments and the flexible member may assist in retaining the segments in the first position. The flexible member may assist in preventing twisting between adjacent segments.

The end portion may include a linkage connected to the retractor at regions co-extensive with the general longitudinal extent of the intermediate portion of the retractor in both the first and second positions. The linkage connection to the retractor may be pivotal connection. The linkage may include a further pivot connecting two links, the further pivot being arranged to be located outside of the general longitudinal extent of the intermediate portion in the second position. At least one of the connections of the linkage to the retractor may be movable translationally in the general direction of the longitudinal extent of the intermediate portion when moving the end portion from the first to the second positions.

The retractor may include a rod arranged to accommodate the majority of the linkage when in the first position. The rod may include a slit.

The retractor may include a pair of linkages and the linkages may include a common connection to the retractor.

According to another aspect of the present invention, a method of operating a surgical retractor comprises passing an end portion and an intermediate portion of the retractor through a restricted opening into a body cavity in a generally linear direction with the end portion then being moved from a first position to a second position, in which the end portion may not be retracted in a generally linear direction through the restricted opening in the body cavity, upon operation of an actuator of the retractor located on the outside of the body cavity.

The end portion may be moved from the first position to the second position by moving a lever between two positions. Alternatively the end portion may be moved from the first to the second position by rotating a member and causing translational movement.

The actuator may cause a connector to move relative to the intermediate portion and the connector may move by sliding within the retractor.

The method may comprise the actuator causing a flexible connector to have its tension increased when moving the end portion from the first to the second position. When the tension on the flexible connector is increased adjacent segments may be arranged to co-operate or co-operate further with each other. A plurality of segments may be caused to co-operate with each other by a co-operating portion of at least one of the segments which extends at an angle to the generally longitudinal extent of the retractor when in the first position to abut, possibly directly, an adjacent portion in the second position. The segments may be caused to rock relative to each other when moving from the first to the second position.

The method may comprise maintaining the orientation of adjacent segments when in the first position by a flexible member which extends between adjacent segments either in the longitudinal extent of the intermediate portion or in a rotational sense about that direction or both.

The method may comprise causing a linkage to pivot when moving the end portion from the first to the second position. The method may comprise causing a linkage to move from a position in which it lies substantially within the extent of the intermediate portion in the longitudinal direction when in the first position to a position in which substantially the whole linkage extends beyond the general extent of the intermediate portion in the longitudinal direction.

The present invention also includes moving the linkage from the second to the first position.

According to a further aspect of the present invention a surgical instrument includes an elongate portion arranged, in use, to be inserted through a restricted opening into a body cavity, the elongate portion comprising a plurality of segments movable relative to each other from a first to a second position whereby, when movement of the segments occurs from the first to the second position the relative direction in which a part of the elongate portion extends when compared to another part of the elongate portion is altered.

The segments may be comprised by separate pieces.

The segments may co-operate with each other when moving from the first to the second position. The segments may co-operate directly with each other.

The segments may be guided during at least part of their movement from the first to the second position.

The segments may co-operate with each other when in the second position to inhibit movement relative to each other in at least one direction transverse to the longitudinal extent of the elongate member.

A number of segments may be provided which are movable relative to each other from the first position to the second position whereby, when such movement occurs relative movement between an intermediate segment and an adjacent segment on one side is arranged to be in a first direction relative to the longitudinal extent of the elongate portion and relative movement between the intermediate segment and an adjacent segment on the other side is arranged to be in a second direction extending at an angle to both the first direction and the longitudinal extent of the elongate portion.

When the instrument is in the first position, the elongate portion may extend in a generally straight direction.

When the segments are in the second position the elongate portion may curve through more 45° or 90° or 120° or in the region of 180° or more.

In the second position, the elongate portion may form a constriction.

The segments may be arranged to be biased towards each other in order to move from the first to the second position. The segments may be arranged to be biased towards each other by a flexible member and the flexible member may extend through the segments. The flexible member may be arranged to be caused to be placed in tension by control means located outside of a body when, in use, the segments are located within a body.

In the second position, further movement of the segments away from the first position may be inhibited, for instance by the segments contacting abutments. The abutments may be provided on adjacent segments. When the segments are urged towards each other from the first to the second position, the force urging the segments towards each other may be arranged to act between two locations where a segment contacts abutments.

The cross-sectional area of the instrument in a direction perpendicular to the extent of the longitudinal portion may remain largely unchanged along the longitudinal extent in both the first and second positions.

The segments may be located at an intermediate portion along the elongate portion. Alternatively or additionally the segments may be located towards the end of the elongate portion.

An extent of the elongate portion may be covered with a protective layer and the extent of the elongate portion which is covered by the protective layer may be substantially the complete extent.

A mechanism may be connected to one of the segments along the elongate portion.

Substantially the complete extent of the elongate portion may be comprised by segments movable relative to each other from the first to the second position.

According to a further aspect of the present invention a surgical instrument includes an elongate portion arranged, in use, to be inserted through a restricted opening in a body, the instrument including a mechanism on a part of the elongate portion, the direction in which the mechanism faces with respect to another part of the elongate portion being variable when the mechanism is located within a body.

The mechanism may be located at the end of the elongate portion.

The mechanism may comprise gripping means or cutting means.

The mechanism may be operable from a portion of the instrument located on the outside of a body when the mechanism is located within a body.

The mechanism may be operable by causing movement of an elongate flexible member along the extent of the elongate portion.

The mechanism may be operable by causing movement of the elongate flexible member along the extent of the elongate portion within the elongate portion.

According to another aspect of the present invention a surgical instrument includes an elongate portion arranged, in use, to be inserted through a restricted opening in a body, the elongate portion being arranged to occupy a first condition in which the elongate portion is flexible along its length and a second condition in which the elongate portion is set in position along its length.

The elongate portion may be comprised by a plurality of segments along its length.

The elongate portion may be arranged to be moved from the first condition to the second condition by control means located outside of a body within which the elongate portion is located.

In the second condition, the elongate portion may be set in position relative to the elongate extent of the elongate portion in two directions along the extent of the elongate portion.

According to another aspect of the present invention a method of using a surgical instrument comprises inserting an elongate portion of the instrument through a restricted opening in a body and moving a plurality of segments of the elongate portion from a first to a second position to cause the relative direction in which a part of the elongate portion extends to be altered.

The method may comprise altering the relative direction in which the end portion of the elongate portion extends when moving the elongate portion from the first to the second position.

The method may comprise altering the relative direction in which the intermediate portion of the elongate portion extends when moving from the first to the second position.

The method may comprise locking the segments in the second position.

The method may comprise moving the segments from the second to the first position prior to withdrawing the elongate portion through the restricted opening.

The method may comprise causing the elongate extent of the elongate portion to undergo a change in at least two relative directions when moving from the first to the second position.

The method may comprise causing the end part of the elongate portion to come back and face at least partly towards the restricted opening when moving from the first to the second position.

The method may comprise causing the elongate portion to at least partially surround and grip a part within the body when moving from the first to the second position.

The method may comprise operating a mechanism connected to the elongate portion when the elongate portion is in the second position.

According to another aspect of the present invention a method of using a surgical instrument comprises inserting an elongate portion of the instrument through a restricted opening in a body, altering the direction in which a mechanism on the elongate portion extends and operating the mechanism.

The method may comprise operating a gripping or a cutting mechanism.

According to a further aspect of the present invention a method of holding a first part of a body away from a second part of a body comprises inserting an elongate portion of a surgical instrument through a restricted opening in a body and causing the elongate portion to go from having a first condition, in which the elongate portion is flexible along its length, to a second condition in which the elongate portion is set in position along its length and holds the first part of the body away from the second part.

The method may comprise urging the first part of the body away from the second part as the elongate portion goes from occupying the first condition to the second condition.

The method may comprise causing the first part of the body to move away from the second part after the elongate portion goes from occupying the first condition to the second condition.

The method may comprise inserting elongate portions from a plurality of surgical instruments through separate restricted openings and causing each portion to go from having the first condition to having the second condition.

The present invention includes any combination of the herein referred to features or limitations.

BRIEF DESCRIPTION OF DRAWINGS

The present invention may be carried into practice in various ways, but various embodiments will now be described by way of example and with reference to the accompanying drawings, in which:

FIGS. 5A and 5B are a front view and a front sectional view respectively of a surgical retractor 4 with an end 5 in an extended position;

FIG. 6 is an enlarged discontinous view showing the blade joints of the end 5 of the connector shown in FIGS. 5A and 5B;

FIGS. 23A and 23B are a perspective side view and a sectional view of an eye at the end of ligature insertion apparatus.

DETAILED DESCRIPTION OF DRAWINGS

Figure 1:
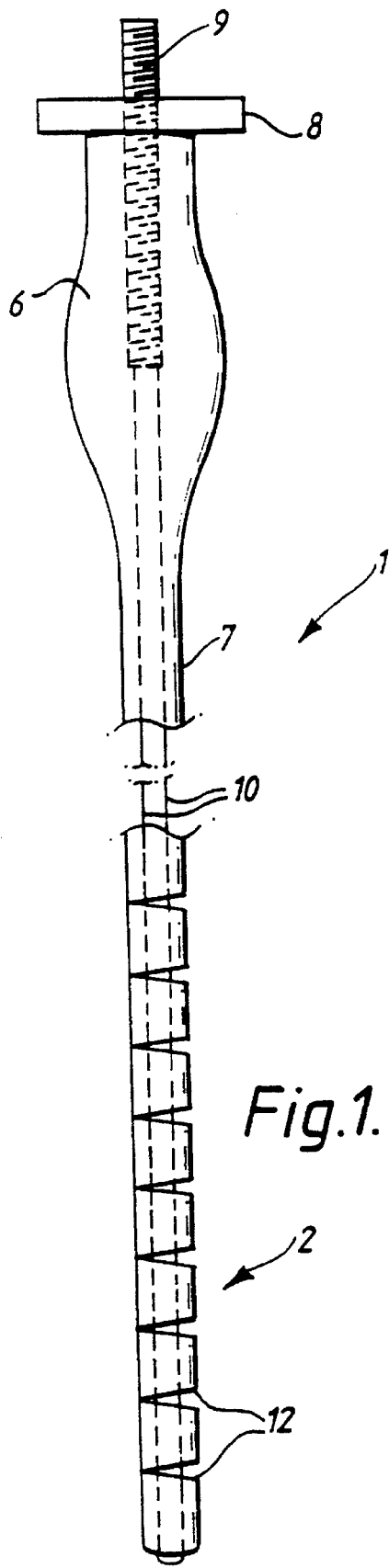
FIG. 1 is a side view of a first embodiment of a surgical instrument comprising a surgical retractor 1 with an end 2 in a straight configuration.

FIG. 1 shows a retractor 1 having a handle 6 which is connected to the end 2 via a hollow rod 7. In use, with the end in the configuration shown in the drawing, the end 2 and part of the rod 7 are fed through a tube in the abdominal wall. The surgeon is then able to manipulate the retractor by the handle 6 and change the configuration of the end 2 into the straight hook shape shown in FIG. 2 by rotating a knurled actuating nut 8.

The nut 8 is threadably connected to a screw member 9 whereby, when the nut 8 is rotated in a clockwise direction, looking from the free end of the handle, the screw member 9 is caused to move translationally away from the end 2. A loop of wire 10 is connected at its free ends to the member 9, and both sides of the loop pass through openings 11 in each segment 3. Accordingly as the wire 10 moves further into the rod 7 the segments are caused to tighten against each other.

As the segments 3 bear against each other they are caused to move out of the axial extent of the rod as the end faces 12 of each segment are formed at a slight angle to the perpendicular to the axis of the rod. In FIG. 1 the upwardly facing surfaces of each segment are parallel with each other as are the downwardly facing surfaces. Accordingly adjacent faces come into abutment with each other as the wire is tightened, and they take up the configuration shown in FIG. 2 in which a straight, substantially rigid hook which subtends approximately 180° is formed. Accordingly in the position shown in FIG. 1, each face extends at an angle of approximately 10° to the axis of the tube.

Figure 3:
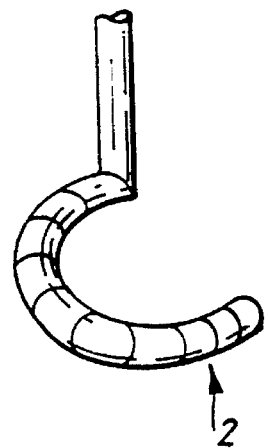
FIG. 3 is a view of an end 2 of a retractor similar to that shown in FIG. 1 in an angled hook configuration.
Figure 4:
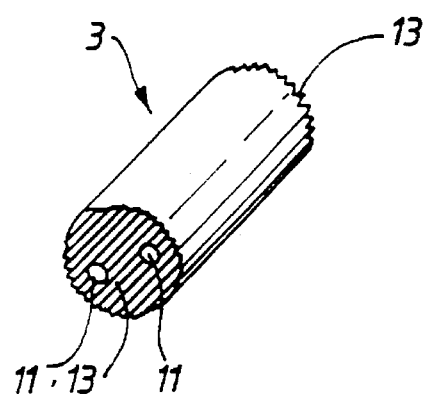
FIG. 4 is a schematic perspective view of one of the segments 3 at the end 2 of the retractor shown in FIG. 1.

In order for the segments to take up the shape shown in FIG. 3, in which a substantially rigid hook which subtends approximately 180° in a direction generally at right angles to the axis of the rod, the face of at least one of the segments is angled differently. For instance, when the end 2 is in the relaxed position and extends generally in line with the axis of the rod 7, the uppermost segment faces the rod with a face extending at 45° to the axis of the rod, and the rod may be correspondingly angled at its end. Thus when the wire is tightened, the segment adjacent to the rod is caused to turn through 90°. The remaining upper and lower faces of the other segments may be parallel to each other in the configuration shown in FIG. 1 as previously described.

Figure 2:
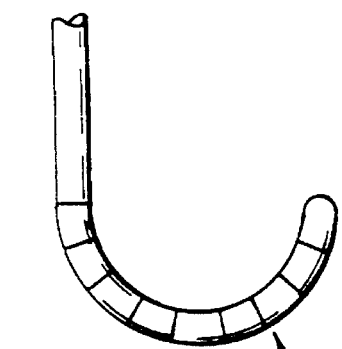
FIG. 2 is a view of the end 2 of the retractor shown in FIG. 1 in a straight hook configuration.

The hooks shown in FIGS. 2 and 3 can be used quickly and conveniently to displace or hold the organs in the required position.

To release the segments from the configuration shown in FIGS. 2 or 3 the nut 8 is rotated in the opposite direction to release the tension in the wire. The wire is sufficiently strong, and the distance between the segments sufficiently small for the flexure of the wire to hold the segments generally straight for ease of insertion or removal when the hook configuration is not required. As the wire is threaded through two openings in each segment the strength of the wire and the close proximity of the segments prevents any significant relative turning of the segments around the longitudinal extent of the end 2.

The face of each segment which is caused to abut against another part of the retractor when in the hook configuration is formed with styrations 13 which are parallel to each other and parallel to adjacent styrations such that co-operating faces do not tend to slip in a rotational or translational sense.

Alternatively an arrangement as in FIG. 12 can be used to restrain such movement.

The retractor 4 shown in FIGS. 5A and 5B includes a shaft 14 which connects to an operating mechanism (not shown). The end 5 includes a linkage which, as shown in FIGS. 5A and 5B, includes opposed cross members 16 extending out at approximately 90° to the axis of the tube from a pivot pin 15 and a pair of supports 17 extending back along and into the shaft 14 from the proximal end of the respective supports 17. In the illustrated position, the retractor can be used in an abdominal cavity to displace or retain organs.

In order to move the retractor from the position shown in FIGS. 5A and 5B to a position in which the members 16 and the supports 17 lie within the area bounded by the shaft 14, an extension of an handle is used to slide a rod 23 away from the working end of the instrument.

The handle which can be pushed or operated by a lever mechanism from outside of a cavity within which the end 5 is located, is connected to a rod 23 which can slide within substantially the whole length of the shaft. When the rod 23 is slid within the shaft away from the working end, a pivot pin 23A at the end 5 is caused to move away from the working end. The pin 23A also extends through and pivotally connects each of the supports 17 and accordingly their ends are caused to move further into the shaft. Pivots 24 also connect the supports 17 to the members 16, and the members 16 are in turn connected by a pin 15 to the end of the shaft 14. Accordingly the members 16 pivot inwardly and the supports 17 slide and move in until they all lie substantially within the extent of the rod 14 in a "collapsed" condition.

In order for the members 16 and the supports 17 to be able to lie within the shaft 14, a slot 26 extends across the end of the shaft as shown in FIG. 6. In the position shown in FIG. 6, the member 16 and the supports 17 are in a collapsed position.

Figures 7A, 7B:
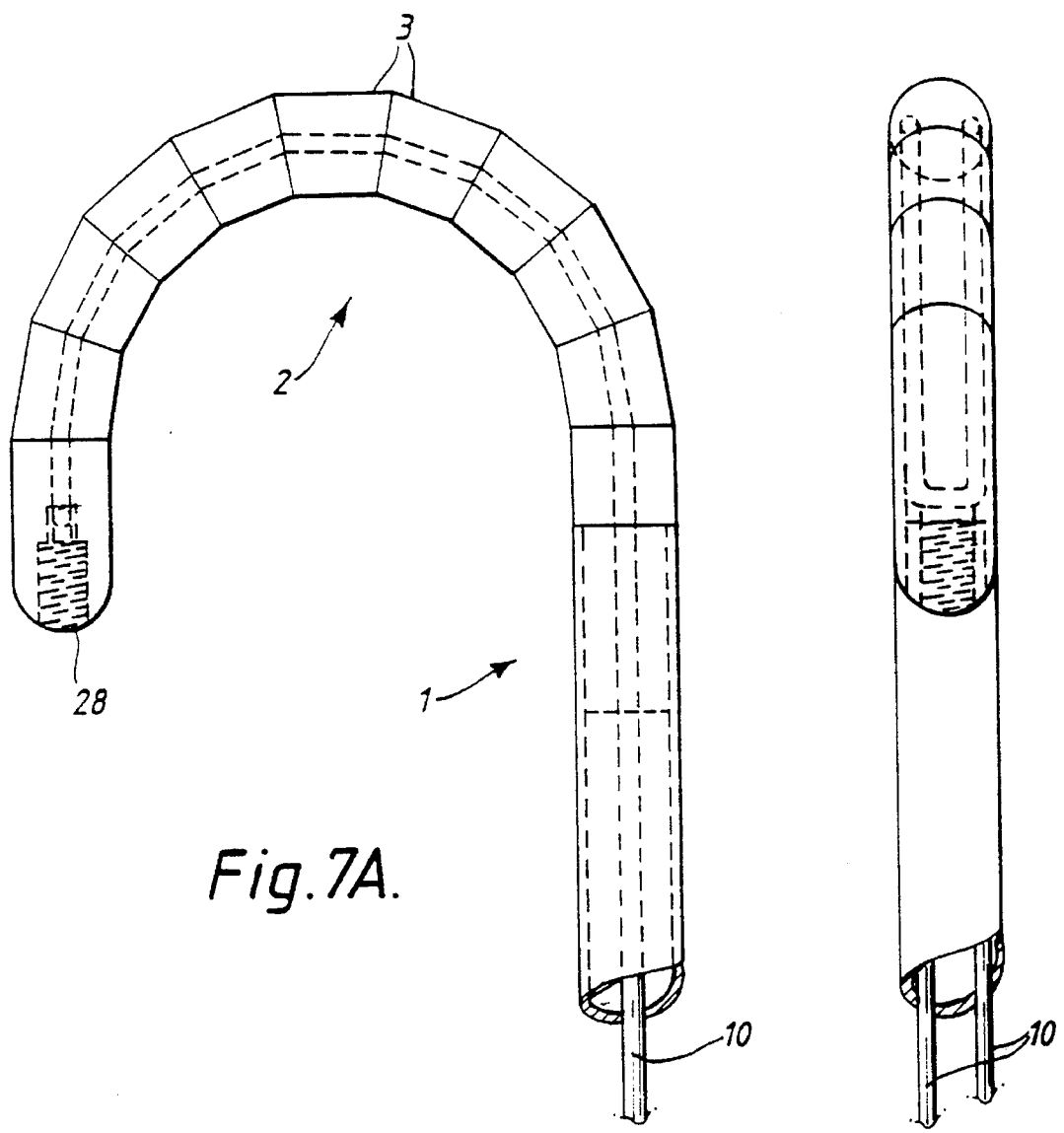
FIGS. 7A and 7B are a side and end view respectively of one end of a retractor in a straight hook configuration.

The embodiment shown in FIGS. 7A and 7B is similar to that shown in FIG. 2 in that it comprises a retractor 2 movable from a straight configuration to the illustrated configuration shown upon effective tightening of both extents of the wire 10.

The end of the retractor is provided with a segment 27 which has a threaded opening 28 at its free end. The wire 10 can be manipulated into position through this opening during assembly of the retractor. That end can be closed by a threaded cap, if desired, to enable the device to present a smooth surface to the body during insertion.

Figure 8:
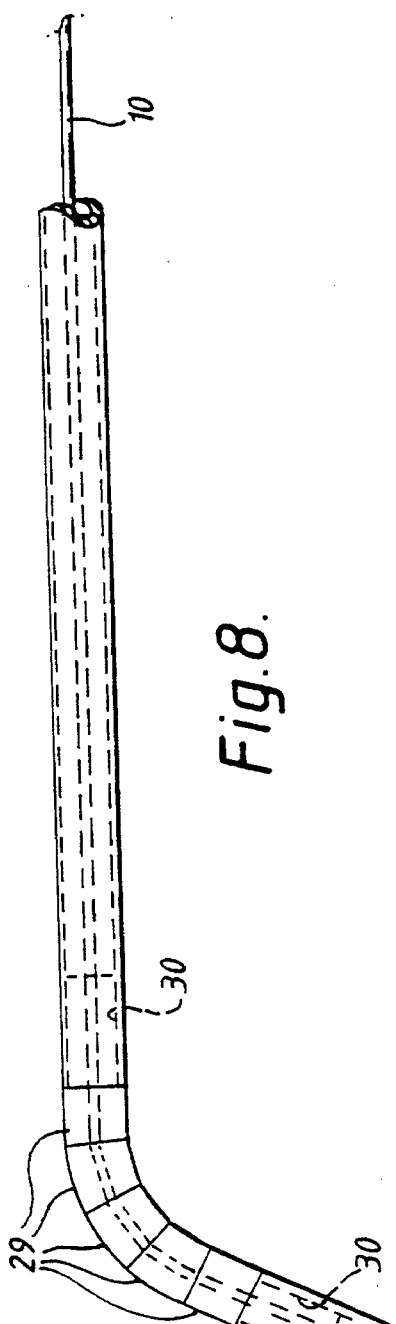
FIG. 8 is a side view of a part of a retractor having an angled section at an intermediate extent of its length.

In FIG. 8, the retractor is provided with five angled segments 29 at an intermediate extent along its extent. Accordingly, when the wire 10 is tightened, the segments take up the position shown. Then end segments in the row are both screwed into the adjacent straight sections along the threaded portion 30 shown.

Figure 9:
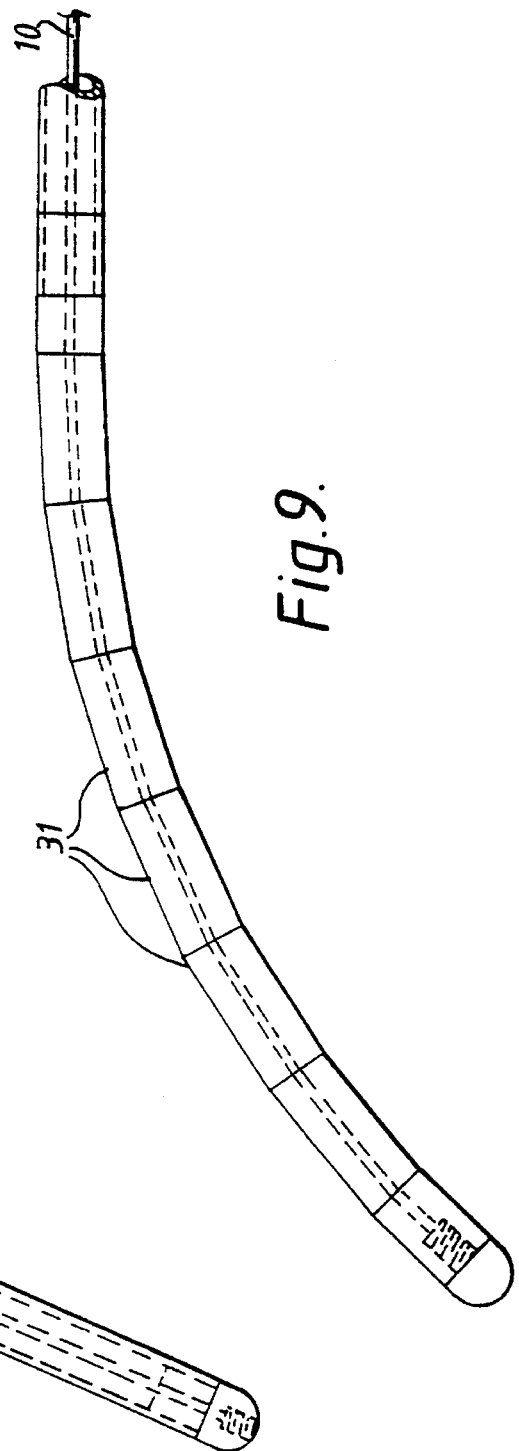
FIG. 9 is a side view of an end of a retractor having a gentle curve.

In FIG. 9, the segments 31 are of a larger extent than the other segments previously described as the retractor is only required to take up the fairly gentle curve shown when tightening the wire 10.

In FIGS. 8 and 9 and other figures, an instrument is shown which undergoes a change in direction in two dimensions only upon tightening of the wire. However, it will be appreciated that the instruments could be modified to undergo a change in direction in three dimensions. Similarly where instruments which undergo a change in direction in three dimensions are shown they could be modified to undergo a change in direction in two dimensions only.

Figure 10B:
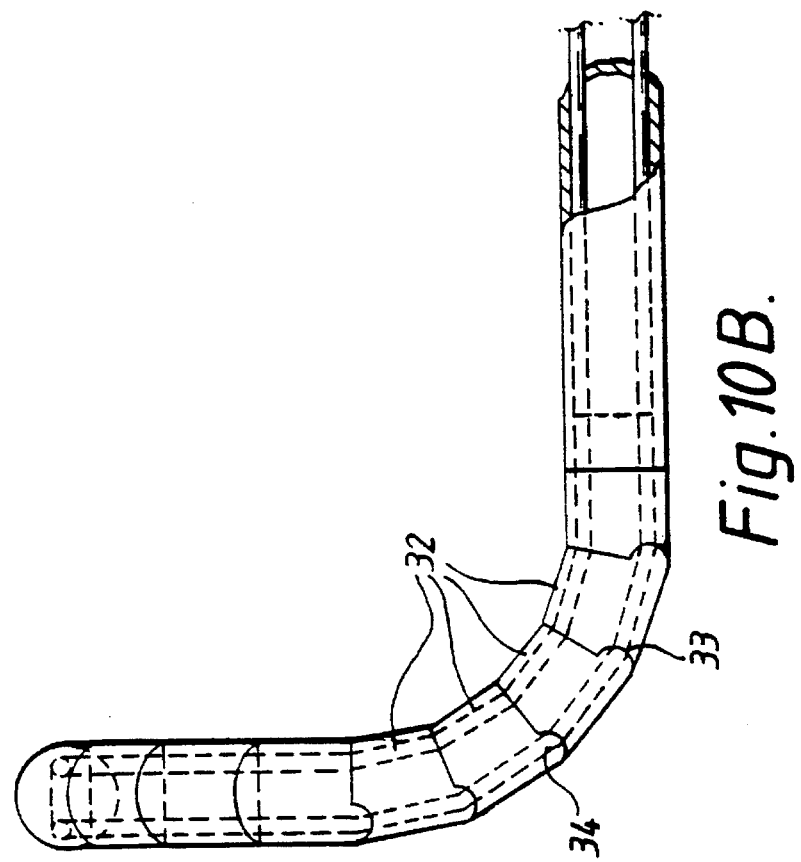
FIGS. 10A and 10B are an underneath and a side view respectively of a retractor having an angled hook configuration.
Figure 10A:
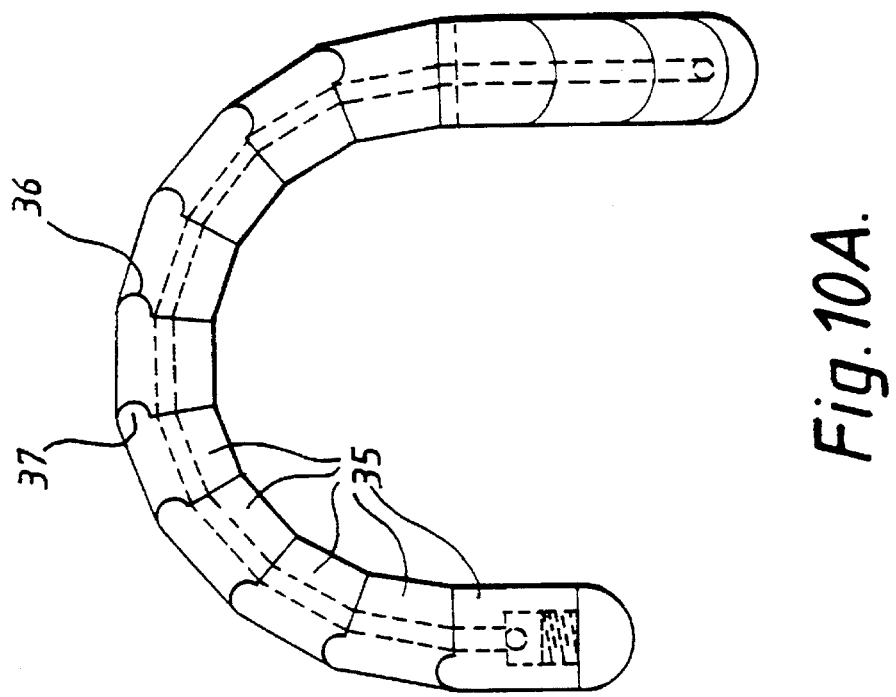

FIGS. 10A and 10B show an angled hook configuration for a retractor similar to that previously described in relation to FIG. 3. The retractor is made up of an initial series of five segments 32 each including a rod section 33 at one end and a socket section 34 at the other end and a further series of segments 35 having a rod section 36 at one end and a socket section 37 at the other where they cooperate with adjacent segments.

Figure 12B:
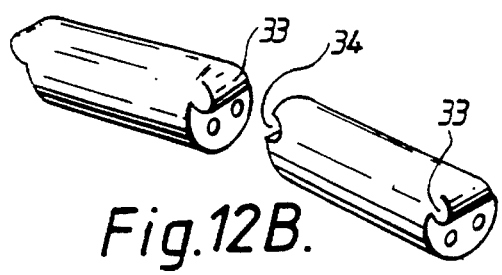
FIGS. 12A and 12B are side and perspective views of two of the segments shown in the retractor of FIGS. 10A and 10B.
Figure 12A:
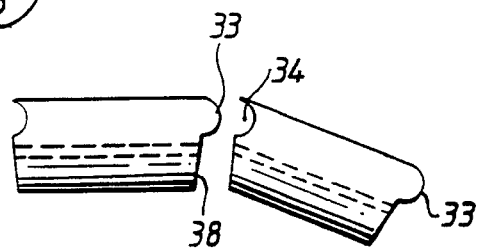

Upon tightening of the wire, the retractor changes from a straight configuration to the curved configuration with each rod section 33 or 36 rocking in an adjacent socket section 34 or 37, as shown in more detail in FIGS. 12A and 12B, until their adjacent angled faces 38 are parallel with each other or abut each other.

The initial series of segments 32 have the longitudinal axes of the rod sections parallel with each other and are configured such that those sections undergo a change in extent along the retractor of 90°, as shown in FIG. 10B. The remaining segments 35 have the longitudinal axes of their rod sections 36 parallel with each other but at right angles to the other section 33. Accordingly the segments 35 undergo a change in angle of 180° with those segments undergoing that change in a direction perpendicular to the change which has occurred for the segments 32. Thus it can be seen that, where the segments 32 and 33 meet, it is necessary for the socket of one of the segments 32 at one end thereof to be at right angles to the rod section at the other end.

Figure 11A:
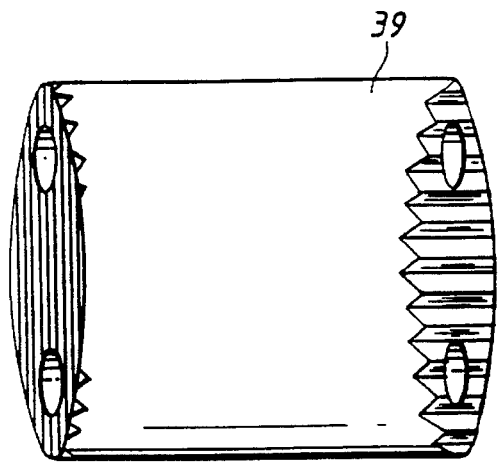
FIGS. 11A, 11B, 11C and 11D are side, plan and end views respectively of a "change over" segment included in the retractor shown in FIGS. 10A and 10B.
Figure 11B:
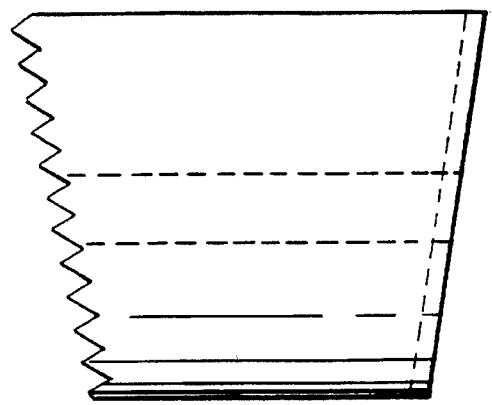
Figure 11C:
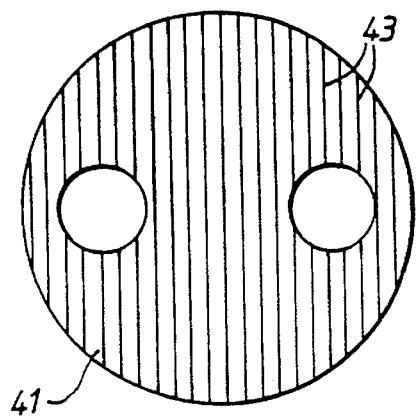
Figure 11D:
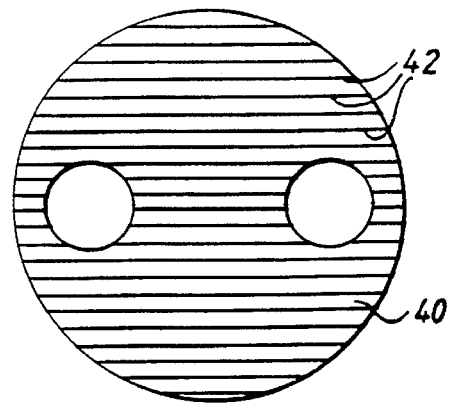

FIGS. 11A, B, C and D show a segment 39 having end faces 40 and 41 respectively which extend at different angles to the longitudinal extend of the segment. The end face 40 has horizontally extending ridges and troughs 42 (when viewed from one side as in FIG. 11D) and the other face 41 has vertically extending ridges and trough 43 (when viewed from the side as in FIG. 11C). These end faces 40 and 41 are arranged, in use, to cooperate with adjacent segments having mating faces with ridges and troughs which extend in the same direction as the face which they are to mate with. Accordingly the segment 39 is used where a change in the direction in which the instrument is extending is desired.

The ridges and trough described herein, and the rod sections and sockets described in relation to FIGS. 10A and 10B give adjacent segments stability in at least one relative direction of possible translational movement. The wire 1 also gives resistant to rotational and translational movement between the segments, when tightened.

Once the principle of being able to change the direction of a generally straight instrument is established, the bent configuration of the apparatus can be designed as required.

Figure 13:
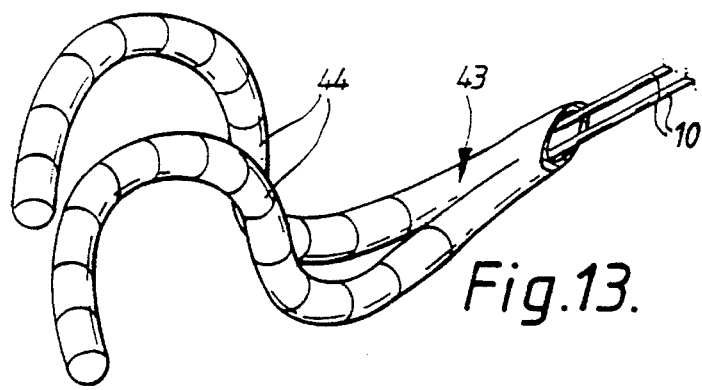
FIG. 13 is a perspective view of a double fork retractor or pusher.

FIG. 13 shows a double fork retractor or pusher 43 in which the tightening of a pair of single wires 10 (as illustrated) or double wires cause two rows of segments 44 to extend at an angle. The wire or wires 10 may act to pull the ends of pairs of wire extending up each row of segments 44 to pull the segments tight.

Figure 14:
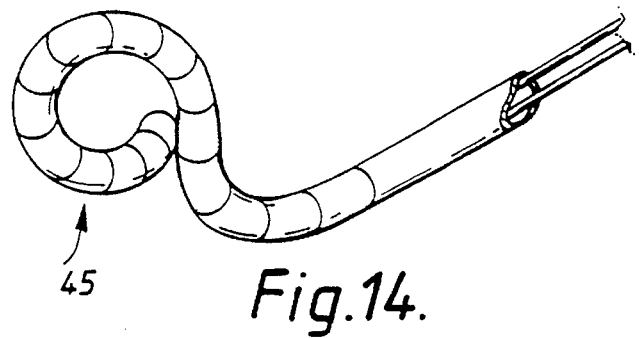
FIG. 14 is a perspective view of a constricting hook.

In the embodiment shown in FIG. 14, the end of the instrument can be made to take up the form of a hook 45 in which the end turns back on itself and the end can be used to choke or grip a part of the body within the surrounded region shown.

Figure 15:
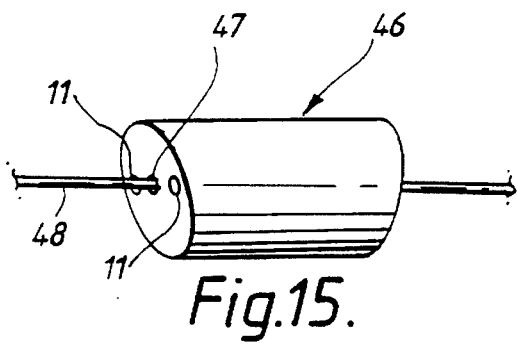
FIG. 15 is a schematic perspective view of a segment in a retractor showing the location of a rigid wire spring.

FIG. 15 shows an angled segment 46 which can be used with any of the retractors or other instruments shown. The segment includes a central opening 47 through which a flexible element 48 passes. The element 48 may be used to import a degree of stiffness between adjacent segments so that when the tension in the conventional wire (not shown) which passes through the openings 11 is relaxed, the element 48 flexes the line of segments towards the position, or to the position in which they extend in a straight line. Alternatively or additionally, the element or filament 48 can be pulled through the openings 47 in aligned segments to operate a mechanism at the end of the instrument, as will be described later in relation to FIGS. 19 to 22.

Figure 16:
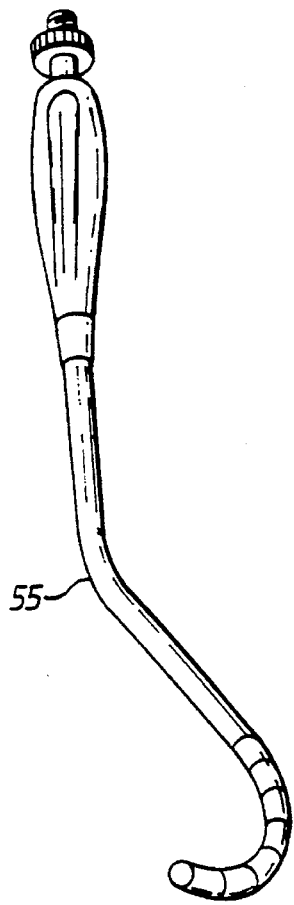
FIG. 16 is a perspective view of a retractor including a straight hook at its end but also having a bent portion at a mid extent.
Figure 17:
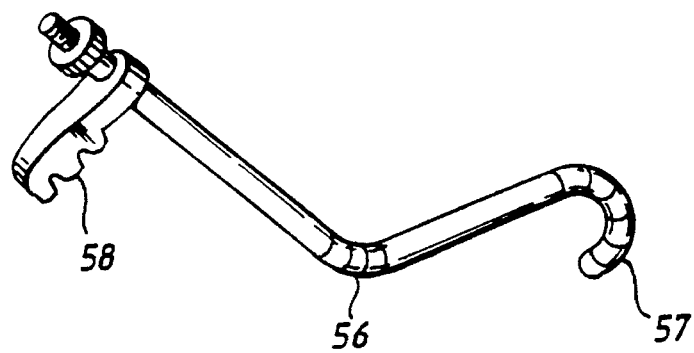
FIG. 17 is a perspective view of a retractor similar to that shown in FIG. 16 with the exception that the intermediate bent portion can be straight during insertion and removal of the retractor.

FIG. 16 shows a retractor having a permanently bent section 55. FIG. 17 shows a retractor which can have a bent section 56 at an intermediate portion in addition to the bent retractor or pusher 57 at the end of the instrument. The instrument of FIG. 17 also has an offset handle 58 which will remain outside of the body cavity and which is of particular use in pelvic surgery.

Figure 18:
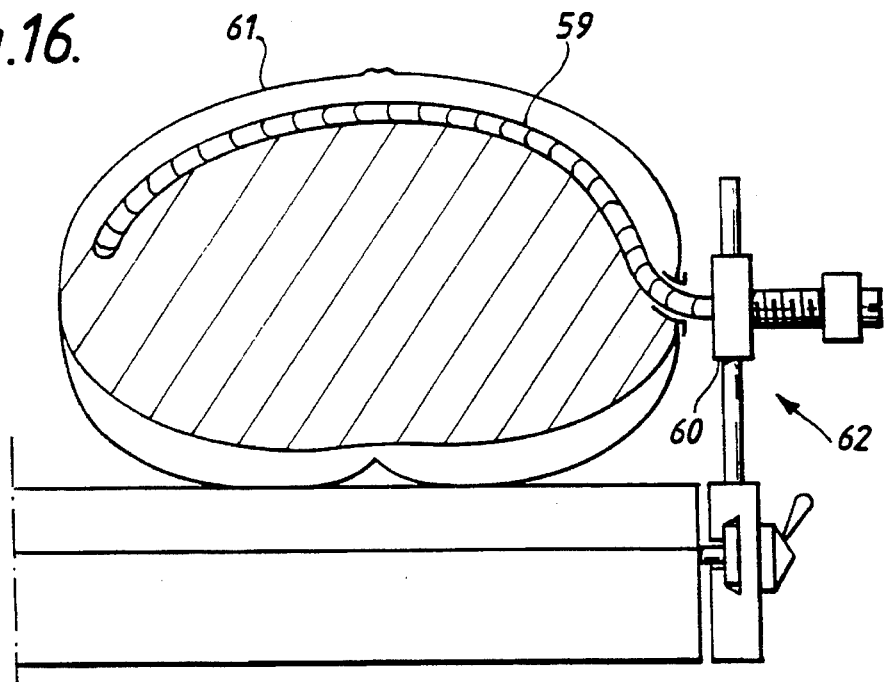
FIG. 18 is a schematic side view of an elongate support member holding a part of a person's body raised up in order to avoid the need for inert gas when performing an operation or examination in a body cavity.

In endoscopic surgery the cavity between the body wall and the organs is created and maintained as a result of a gas pressure. However, it is a considerable problem to try and maintain sufficient pressure as the camera and instruments are being inserted or removed. FIG. 18 shows the use of an artificial "rib" 59 which is inserted through an opening 60 at one side of the body and extends across the body within the cavity and holds the wall 61 away from the organs.

The rib 59 can be inserted in a generally straight direction and then tightened to the position shown to raise the wall away from the organs. Alternatively or additionally, when the rib is locked in the curved configuration shown it can then be maneuvred to raise the body wall clear of the organs.

More than one rib may be provided to raise a whole region of body wall, in which case the ribs may be generally parallel but spaced from each other.

Retaining means 62 may be provided to hold the ribs in the required position during an operation.

With such a rib or ribs, the operation may be performed with low or no excess gas pressure within the cavity.

With the illustrated rib, four openings may be equispaced around the longitudinal extent of each segment of the retractor with a pair of wires passing through those openings and around the end of the rib. Having an extent of wire through each of the openings increases the strength of the rib, particularly where the wires are under tension and retains the rib in the bent configuration with more rigidity than is achieved with a single wire passing through diametrically opposite openings.

Figure 19:
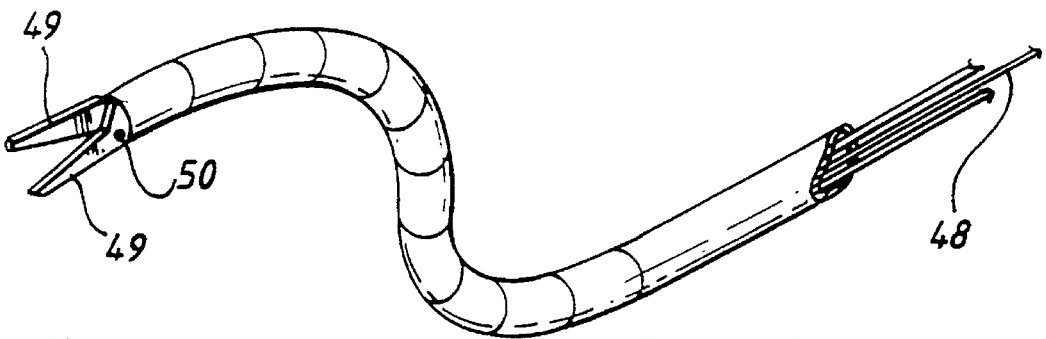
FIGS. 19, 20 and 21 are schematic perspective views showing the end of an instrument having scissors, a needle holder and gripping forceps located at the free end thereof.

In FIG. 19 the end of the instrument includes a pair of blade members 49 either or both of which can be pivoted about an axis 50 to move the blade members towards each other either to cut, or to compact the end to allow insertion and removal through the narrow body wall passage. The central filament 48 actuates the or each blade member at the required time. Release of tension allows or causes the blades to return to the position illustrated. Return of the filament 48 may cause or assist in divergence of the blade member or, alternatively or additionally resilient means such as a spring may cause or assist in the blade members moving relative to each other to a closed or open position.

Figure 20:
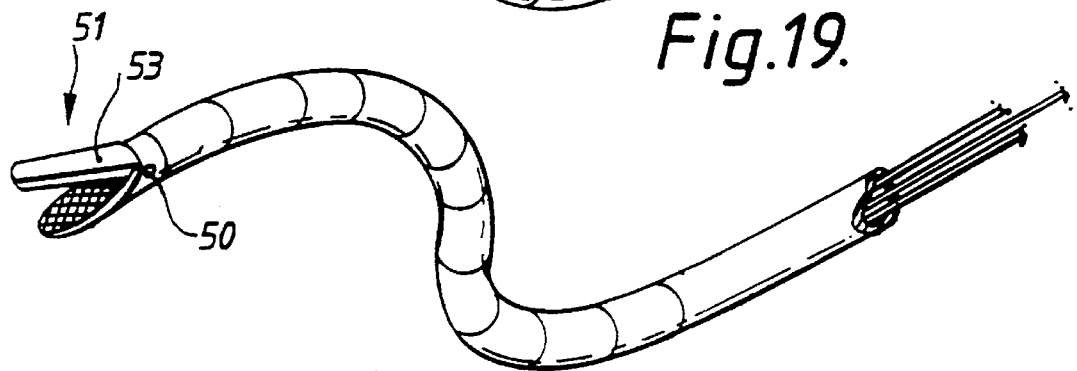
Figure 21:
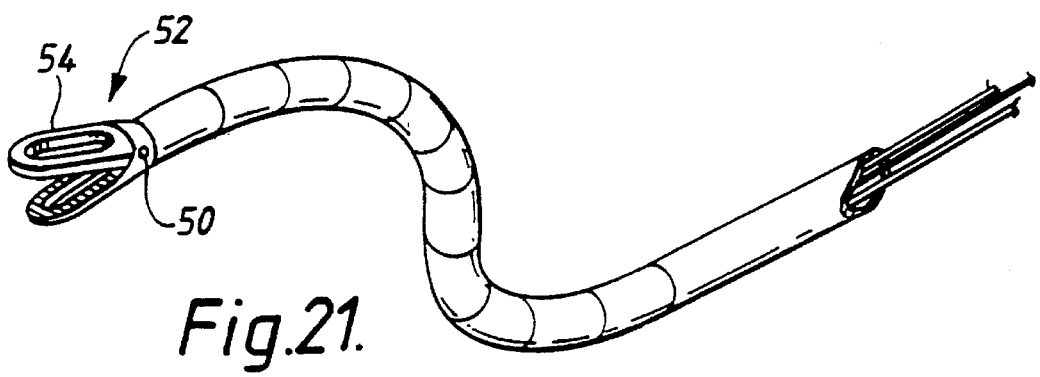

In the embodiment shown in FIGS. 20 and 21 a needle holder 51 and a forcep grasper 52 respectively are shown at the end of the instruments. A pivotal member 53 or 54 is movable about the axis 50 to enable a needle or forcep to be gripped as required. Movement and maintaining the pivotal members 53 and 54 is as described above with regard to the relative pivotal movement of the blade members in FIG. 19.

Figure 22:
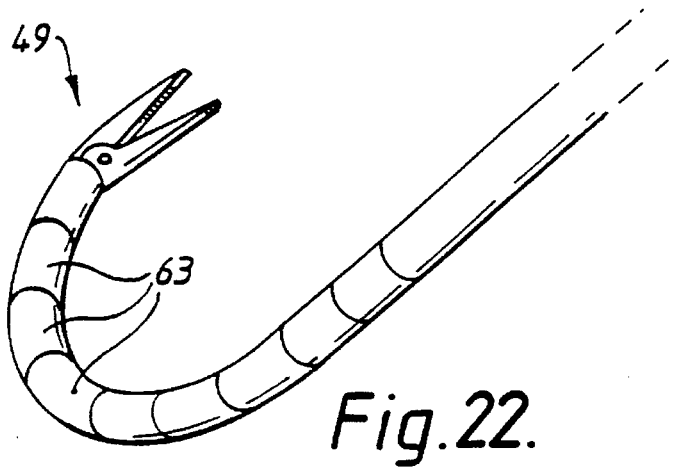
FIG. 22 is an end view of an instrument showing the forceps, needle holders or scissors facing back towards the direction into which they have been inserted into the body cavity.

FIG. 22 shows an instrument having a pair of blade members 49, as shown in FIG. 19. The segments 63 are angled relative to each other such that after the wire has been tightened to cause the segments to extend in a curve, the blade members extend in substantially the opposite direction to that in which they extended during insertion through the body wall. The blade members are operable by tightening a flexible cord or filament which extends through a central opening in each segment, as previously described.

It will be appreciated that the blade members could be replaced by other tools such as forcep or needle holders which return to or face back towards the person holding the remote end of the instrument.

FIGS. 23A and 23B show the end of an instrument which may be curved after insertion into a body cavity being provided with an eye or formination 64 for ligature or thread access or return.

Any of the instruments described may have a complete or partial waterproof sleeve or plastic sheath, if desired. The sleeve or sheath may assist in preventing snagging of the instrument during insertion, or contamination of the body or instrument and may assist in flexing the instrument back towards a straight configuration when the tension in the wires is released.

In all of the herein described embodiments an instrument which is able to be inserted through a tube and is also able to take up a configuration in which it extends beyond the region bounded by the tube used to introduce it is provided, with a rigid configuration if necessary.

What we claim is:

1. An endoscopic surgical instrument including an elongate portion comprising a plurality of segments, said elongate portion being arranged, in use, to be inserted through a restricted opening in a body when in a first position, said segments being pivotally movable relative to each other with adjacent segments being movable about a pivot located towards a first side of the instrument from said first position to a second, substantially rigid predetermined position upon pulling of a control means extending within the elongate portion, said control means being located towards a second side of the instrument opposite to said first side whereby, when movement of the segments occurs from said first position to said second position the relative direction in which a part of the elongate portion extends, when compared to another part of the elongate portion, is altered and in which, when said segments are held in said second predetermined position, further movement of said segments away from said first position is arranged to be inhibited by one segment being pulled against an abutment associated with an adjacent segment by the control means.

2. A surgical instrument according to claim 1 including separate pieces, said pieces comprising said segments.

3. A surgical instrument according to claim 1 in which said segments abut each other when in said second position.

4. A surgical instrument according to claim 1 in which said segments include an intermediate segment and an adjacent segment on one side of said intermediate segment and an adjacent segment on the other side of said intermediate segment said intermediate segment and said adjacent segments being movable from the first position to the second position whereby movement of those segments from the first to the second position causes relative movement between said intermediate segment and said adjacent segment on one side to be in a first direction relative to the longitudinal extent of the elongate portion and relative movement between said intermediate segment and said adjacent segment on the other side to be in a second direction extending at an angle to both said first direction and the longitudinal extent of the elongate portion.

5. A surgical instrument according to claim 1 in which, in the second position, said elongate portion forms a constriction.

6. A surgical instrument as claimed in claim 1 in which the segments are arranged to be biased towards each other in order to move from the first to the second position.

7. A surgical instrument according to claim 1 in which the cross sectional area of the instrument, in a direction perpendicular to the extent of the longitudinal portion, remains largely unchanged along the longitudinal extent in both the first and second positions.

8. A surgical instrument according to claim 1 in which segments are located at an intermediate position along the elongate portion.

9. A surgical instrument according to claim 1 including a protective layer with an extent of the elongate portion being covered with said protective layer.

10. A surgical instrument according to claim 1 including a mechanism said mechanism being connected to one of the segments on the elongate portion.

11. A surgical instrument according to claim 1 arranged, in use, to be inserted through a restricted opening in a body, the instrument including a mechanism, said mechanism being located on a part of said elongate portion, the direction in which said mechanism faces with respect to another part of said elongate portion being variable when said mechanism is located within a body.

12. A surgical instrument according to claim 11 in which said mechanism comprises gripping means.

13. A surgical instrument according to claim 11 in which said mechanism comprises cutting means.

14. A surgical instrument according to claim 11, including operating means, said mechanism being operable by said operating means, said operating means being located on the outside of a body when said mechanism is located within a body.

15. A method of using a surgical instrument in endoscopic surgery comprising an elongate portion which includes a plurality of segments said method comprising the steps of: inserting said elongate portion of said instrument through a restricted opening in a body when in a first position and moving a plurality of said segments of the elongate portion from said first position to a predetermined second position by pulling a control means extending within the elongate portion and located towards one side of the instrument to cause the relative direction in which a part of said elongate portion extends to be altered by adjacent segments pivoting relative to each other towards the other side of the instrument, holding the segments substantially rigid in the second position and contacting an abutment by pulling at least one segment against the abutment by the control means to inhibit further movement of the segments away from the first position and to hold the segments substantially rigid.

16. A method according to claim 15 comprising altering the relative direction in which an intermediate portion of the elongate portion extends when moving from the first to the second position.

17. A method according to claim 15 comprising causing said elongate extent of said elongate portion to undergo a change in at least two relative directions when moving from the first to the second position.

18. A method according to claim 15 comprising causing the end part of said elongate portion to come back and face at least partly towards the restricted opening when moving from the first to the second position.

19. A method according to claim 15 comprising operating a mechanism connected to the elongate portion when the elongate portion is in the second position.

* * * * *